US006489303B2

(12) United States Patent
Jancys

(10) Patent No.: US 6,489,303 B2
(45) Date of Patent: Dec. 3, 2002

(54) ANTHELMINTIC COMPOSITION

(75) Inventor: Arunas H. Jancys, Auckland (NZ)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 09/973,361

(22) Filed: Oct. 9, 2001

(65) Prior Publication Data

US 2002/0081292 A1 Jun. 27, 2002

(30) Foreign Application Priority Data

Oct. 10, 2000 (NL) ................................. 507445
Oct. 11, 2000 (NL) ................................. 507479

(51) Int. Cl.$^7$ ........................ A01N 43/04; A01N 43/40; A01N 43/78; A01N 43/52; A01N 35/02
(52) U.S. Cl. .......................... 514/30; 514/52; 514/355; 514/367; 514/393; 514/394; 514/395; 514/694
(58) Field of Search ........................ 514/30, 52, 355, 514/367, 393, 394, 395, 694

(56) References Cited

U.S. PATENT DOCUMENTS 6,340,672 B1 * 1/2002 Mihalik ........................ 514/30

FOREIGN PATENT DOCUMENTS

| EP | 0 329 460 B1 | 5/1992 |
| EP | 0 170 006 B1 | 7/1992 |
| GB | 2 166 436 A | 5/1986 |
| GB | 2 176 182 A | 12/1986 |
| GB | 2 187 742 A | 9/1987 |
| GB | 2 192 630 A | 1/1988 |

* cited by examiner

*Primary Examiner*—Kevin E. Weddington
(74) *Attorney, Agent, or Firm*—Joseph M. Mazzarese

(57) ABSTRACT

An anthelmintic composition including an Antibiotic S541 compound or a chemical derivative thereof, together with an insoluble anthelmintic compound. The composition is stabilized by between about 0.15% and about 5.0% of an antioxidant by weight of the total composition.

17 Claims, No Drawings

ANTHELMINTIC COMPOSITION

TECHNICAL FIELD

The invention relates to stable anthelmintic compositions combining two or more active compounds.

BACKGROUND ART

When formulating anthelmintic compositions it is necessary that the compositions maintain the stability of the active compounds in those compositions. In particular, it is necessary to maintain the stability in order to allow for the compositions to be prepared well in advance of their intended use.

UK Patent Specifications 2166436, 2176182 and 2187742 and EP170006 describe antibiotic compounds, designated Antibiotics S541, prepared by fermentation of Streptomyces microorganisms and chemical derivatives thereof. The disclosure of these UK and EP documents are incorporated herein by reference. Such compounds have antibiotic, and, in particular, anti-endoparasatic, anti-ectoparasitic, antifungal, insecticidal, nematicidal and acaricidal activity and are of special use in agriculture, horticulture and animal and human health. These compounds include the avermectin and milbemycin groups of compounds.

EP329460 discloses that the stability of these antibiotic compounds can be enhanced when they are in the presence of an antioxidant. In particular, EP329460 refers the stabilisation of a group of Antibiotic S541 derivatives described in UK2192630A and in particular to 23[E]-methoxyimino Factor A, also known as moxidectin. A variety of antioxidants are disclosed in EP329460 as useful for stabilisation (which are herein incorporated by way of reference) with particular reference to butylated hydroxytoluene (BHT). These antioxidants are disclosed as being present in amounts ranging from 0.005 to 1% with respect to the antibiotic compounds.

It has now been discovered that these antibiotic compounds may be unstable when in the presence of an antioxidant as described in EP329460, when the antiobiotic compounds are combined with another active material to form a combination anthelmintic composition.

OBJECT OF THE INVENTION

It is an object of the invention to provide a stable anthelmintic composition including antibiotic compounds as described above together with other active compounds.

Other objects of the invention will be apparent to those skilled in the art from the description and examples provided herein.

SUMMARY OF THE INVENTION

In broad terms, according to one aspect of the invention, there is provided an anthelmintic composition including an avermectin or a milbemycin, together with praziquantel, wherein the composition is stabilised by between about 0.15% and about 5.0% of an antioxidant by weight of the composition.

In broad terms, according to another aspect of the invention, there is provided an anthelmintic composition combining an Antibiotic S541 compound preparable by fermentation of a Streptomyces microorganism, or a chemical derivative thereof, and another anthelmintically active compound, wherein the composition is stabilised by between about 0.15% and about 5.0% of an antioxidant by weight of the total anthelmintic composition.

In broad terms, according to a further aspect of the invention, there is provided a method of stabilising an anthelmintic composition which combines an Antibiotic S541 compound preparable by fermentation of a Streptomyces micro organism, or a chemical derivative thereof, and another anthelmintically active compound, the method including the addition of between about 0.15% and about 5.0% of an antioxidant by weight of the total composition.

Preferably the amount of the antioxidant is between about 0.2% and about 3.0% by weight of the total composition and more preferably is between about 0.2% and 0.3% by weight of the total composition. Most preferably the amount is 0.25% by weight.

Preferably the amount of antioxidant is in addition to antioxidant used to stabilise the Antibiotic S541 compound or derivative prior to its inclusion in the anthelmintic composition.

Preferably the antioxidant is one which is capable of reacting with free radicals and may be a $C_{1-12}$ alkyl gallate, benzyl hydroxybenzoate, butylated hydroxyanisole, butylated hydroxytoluene, quinones and salts thereof, nodihydroguaiaretic acid, or tocopherols.

Preferably the antioxidant is butylated hydroxytoluene (BHT).

Preferably the Antibiotic S541 compound or derivative thereof is an avermectin or a milbemycin.

Preferably the Antibiotic S541 compound or derivative is abamectin, ivermectin, doramectin, selemectin or moxidectin.

Preferably the anthelmintically active compound is an insoluble compound such as praziquantel or an insoluble benzimidazole.

Preferably the composition is an oral drench composition.

In another aspect, the invention may be seen to be an oral anthelmintic drench formulation including moxidectin technical concentrate (MTC) or moxidectin technical material (MTM), and praziquantel, wherein the formulation is stabilised by the inclusion of between about 0.15% and about 5.0% of BHT by weight of the formulation, the BHT being in addition to BHT present in the MTC or MTM.

DETAILED DESCRIPTION

This invention relates generally to improvements in the stability of anthelmintic compositions which include, as one of the active components, the Antibiotics S541 which have been referred to previously herein. As has been stated, the use of antioxidants, such as BHT, to stabilise certain antibiotic compounds is known. This knowledge is used in the preparation of technical material and technical concentrate solutions of antibiotic compounds, such as those derived from the fermentation of Streptomyces microorganisms, and chemical derivatives thereof, which are later used for the preparation of veterinary and human pharmaceutical compositions.

Typical antibiotic compounds of use in the compositions according to the invention are the avermectins (e.g., abamectin, ivermectin, doramectin, selemectin) and the milbemycins (e.g., moxidectin).

A particular example is the production of moxidectin technical material and moxidextin technical concentrate, both of which include between about 0.3 and 0.6% of the antioxidant BHT. This technical material or concentrate can be stored for a suitable length of time in order that commercial products can be prepared which include the active material. For example, the American Cyanamid Company products CYDECTIN® and VETDECTIN® liquid compositions are prepared using moxidectin technical material or moxidectin technical concentrate. Both these commercial products have excellent stability as is well known.

Both CYDECTIN® and VETDECTIN® include one active material, moxidectin, which is stabilised by the BHT originally present in the technical material or concentrate of moxidectin used to produce the commercial product.

It is therefore surprising that when this moxidectin technical material or concentrate is used to produce an anthelmintic composition that combines moxidectin with another anthelmintic compound, suitable stability of the moxidectin was not achieved. This difficulty has been specifically observed when the other anthelmintic compound used in the composition is the insoluble compound praziquantel present in the composition as a suspension. Without wishing to be bound by this, as the other individual components in the formulation are relatively standard in the formulation art, it seems that it may be an effect of the insoluble praziquantel that destabilises the moxidectin. It is also possible that it is an effect of the combination of components required to keep the praziquantel in suspension in the formulation that results in this destabilising effect.

In order to achieve stability of moxidectin to suitable levels (e.g., above 95% for longer than three (3) months) it has been found necessary to include additional amounts of an antioxidant such as BHT into the formulation. A suitable amount of additional antioxidant is above about 0.15% of antioxidant by weight of the total composition and preferably below about 5.0% by weight. More preferably, the amount of BHT added by weight of the total composition is between 0.2% and 3.0% and more preferably between about 0.2% and 0.5% by weight of the composition. Most preferably the amount is about 0.25% by weight.

It is hypothesised that, as other antibiotic compounds in the S541 series can also be stabilised by antioxidants such as BHT, their use with insoluble compounds such as praziquantel will also require additional antioxidant to maintain stability. Further, it is hypothesised that the inclusion of other insoluble anthelmintics, such as the insoluble benzimidazoles, may also affect the stability of the antibiotic compounds when used in combination.

The antioxidant of preferred use in the compositions according to the invention is butylated hydroxytoluene (BHT). Other antioxidants could also include those disclosed in EP329460 such as those which are capable of reacting with free radicals, including a $C_{1-12}$ alkyl gallate, benzyl hydroxybenzoate, butylated hydroxyanisole, quinones and salts thereof, nodihydroguaiaretic acid, or tocopherols.

It is known that compounds such as citric or phosphoric acid can act as synergists for some antioxidants such as butylated hydroxyanisole (BHA). It may be that it is necessary for the compositions to include both the extra antioxidant and citric acid to allow the stability levels needed, to be achieved. Preferably the composition will also include between about 0.1% and 1.5% w/v of citric or phosphoric acid. Such compounds are usually present primarily as a buffering agent.

The invention can therefore also be seen to be directed to a method of preparing a stable composition which combines an Antibiotic S541 compound, or chemical derivative thereof (preferably an avermectin or milbemycin), with another anthelmintically active compound, which is preferably praziquantel, wherein the method includes the step of adding between about 0.15% and about 5.0% by weight of the total composition of an antioxidant, which is preferably BHT. In a preferred form the method will include the addition of moxidictin via moxidectin technical material (MTM) or concentrate (MTC) and the amount of BHT added will be in addition to the BHT originally present in the MTM or MTC. In a further preferred form the method will also include the addition of citric acid.

Where compositions according to the invention are to be used or be prepared for use, in human or veterinary medicine, or in agriculture, horticulture or forestry, they may also contain one or more suitable carriers or excipients as will be known in the art. The compositions are preferably oral drench compositions but could also be formulated as injectables or feed additives as will be known in the art.

EXAMPLES

The following examples illustrate the invention and include a preferred form of the invention. The moxidectin technical concentrate (or moxidectin concentrate) used in the Example formulations contains 0.49% BHT. The praziquantel is in suspension. The examples should not be seen to be limiting.

Example 1

| Method of Manufacture for Moxidectin and Praziquantel Oral Drench | |
|---|---|
| 1. Add to mixing vessel 1: | The amount of Water equivalent to 20% w/v |
| 2. Heat to 70–80° C. | |
| 3. Add to mixing vessel 1: | Disodium Edetate |
| | Methyl Paraben |
| | Propyl Paraben |
| | Polyethylene Glycol 6000 |
| | Polyoxyethylene 40 Stearate |
| | Anti Foam 9020 |
| 4. Mix until homogenous. | |
| 5. Add to mixing vessel 1: | Praziquantel |
| 6. Mix for 30 minutes. | |
| 7. Add to a premix vessel: | Polysorbate 80 |
| | Moxidectin Technical Concentrate |
| | Butylated Hydroxytoluene |
| 8. Mix for 30 minutes until Butylated Hydroxytoluene is dissolved completely. Rinse empty Moxidectin drums and used containers with part of Propylene Glycol and add rinse to premix vessel. | |
| 9. Transfer from premix vessel to mixing vessel 1 with continuous mixing. Rinse the premix vessel with part of Propylene Glycol and add to mixing vessel 1. | |

-continued

| Method of Manufacture for Moxidectin and Praziquantel Oral Drench |
|---|
| 10. Disperse in a premix vessel: Xanthan Gum with Propylene Glycol |
| 11. Mix to a smooth dispersion (maximum 5 minutes) and add to vessel 1 with continuous stirring. |
| 12. Rinse the premix vessel with part of Propylene Glycol and add to vessel 1. |
| 13. Add to Vessel 1 the remaining Propylene Glycol and Water and mix for 20 minutes. |
| 14. Check pH. Adjust pH to the range 6.0–6.8 with 25% w/v Sodium Citrate in Water or 25% w/v Citric Acid in Water. Record final weight and volume. |
| 15. Take appropriate volume of sample to the laboratory for final analyses. |
| 16. Upon laboratory approval, pump through the appropriate filter to the storage tank. Pack according to the Packing Sheet Instructions. |
| 17. Rinse vessel, transfer line storage tank and filler with 2 × 75 L of Propylene Glycol. Store in correctly labelled drums. |

Example II

| Moxidectin/Praziquantel Oral Drench Formulation | | | | | | |
|---|---|---|---|---|---|---|
| | | | | | Batch Size 1000 L Requirements | |
| | | % | Raw Material | | | |
| Ingredient | Amount | Excess | Description | Potency | % w/v | kg |
| Moxidectin | 1.00 mg/mL | 5.0 | Moxidectin Technical Concentrate | 30% | 0.345 | 3.45 |
| | | | Antifoam 9020 | | 0.005 | 0.05 |
| | | | Polysorbate 80 USP or equivalent | | 10.000 | 100.0 |
| | | | Butylated Hydroxytoluene NF or equivalent | | 0.250 | 2.5 |
| | | | Disodium Edetate USP or equivalent | | 0.200 | 2.0 |
| | | | Methylparaben NF or equivalent | | 0.200 | 2.0 |
| | | | Propylene Glycol USP or equivalent | | 10.000 | 100.0 |
| | | | Polyethylene Glycol 6000 NF or equivalent | | 3.000 | 30.0 |
| | | | Polyoxyethylene 40 stearate NF or equivalent | | 2.500 | 25.0 |
| Praziquantel | 18.8 g/L | 5.0 | Praziquantel USP or equivalent | 100% | 1.960 | 19.6 |
| | | | Propylparaben NF or equivalent | | 0.100 | 1.0 |
| | | | Xanthum Gum NF or equivalent | | 0.200 | 2.0 |
| | | | Purified Water USP or equivalent | | 73.24 | 732.4 |
| | | | Sodium Citrate USP or equivalent | | 0.500 | 5.0 |
| | | | Citric Acid USP or equivalent | | * | * |
| Adjust pH if outside the range of 6.0–6.8 with Sodium Citrate/Citric Acid buffer. | | | | Total | 102.5 | 1025.0 |

* Adjust pH if outside the range of 6.0–6.8 with Sodium Citrate/Citric Acid buffer.

Example III

Stability Study Report: Moxidectin and Praziquantel Oral Drench

Tables 1, 2 and 3 give the results for Batches 980213A, V02484/0 and V03307/0 stored in 100% HDPE at 25 C. Each batch was produced according to the formulation and production method disclosed in Examples I and II.

TABLE 1

Batch No. 980213A, Packaged in 100% HDPE bottles, Storage at 25° C.

| Timepoint | Moxidectin (% label claim) Average | Praziquantel (% label claim) Average | Specific Gravity @ 25° C. | pH @ 25° C. |
|---|---|---|---|---|
| Initial | 103.8 | 101.1 | 1.027 | 6.55 |
| 3 months | 98.6 | 99.4 | 1.026 | 6.65 |
| 4 months | 99.5 | 103.5 | 1.026 | 6.51 |
| 5 months | 99.4 | 98.5 | 1.024 | 6.52 |
| 6 months | 99.6 | 103.7 | 1.026 | 6.58 |

TABLE 1-continued

Batch No. 980213A, Packaged in 100% HDPE bottles, Storage at 25° C.

| Timepoint | Moxidectin (% label claim) Average | Praziquantel (% label claim) Average | Specific Gravity @ 25° C. | pH @ 25° C. |
|---|---|---|---|---|
| 10 months | 96.3 | 105.1 | 1.022 | 6.43 |
| 12 months | 94.4 | 104.0 | 1.026 | 6.40 |

TABLE 2

Batch No. V02484/0, Packaged in 100% HDPE bottles, Storage at 25° C.

| Timepoint | Moxidectin (% label claim) Average | Praziquantel (% label claim) Average | Specific Gravity @ 25° C. | pH @ 25° C. |
|---|---|---|---|---|
| Initial | 105.1 | 107.3 | 1.026 | 6.65 |
| 3 months | 102.2 | 100.0 | 1.028 | 6.57 |
| 6 months | 100.3 | 96.5 | 1.036 | 6.52 |
| 12 months | 102.7 | 110.0 | 1.028 | 6.47 |

TABLE 3

Batch No. V03307/0, Packaged in 100% HDPE bottles, Storage at 25° C.

| Timepoint | Moxidectin (% label claim) Average | Praziquantel (% label claim) Average | Specific Gravity @ 25° C. | pH @ 25° C. |
|---|---|---|---|---|
| Initial | 107.0 | 103.9 | 1.028 | 6.63 |
| 3 months | 108.0 | 107.9 | 1.035 | 6.56 |

Discussion

The moxidectin content for this formulation varies in the range 94.4–108.0% of label claim (0.1% w/v) for real time study at 25 C. The acceptable range of results for moxidectin concentration is 95–110% of label claim. Although the moxidectin content is below the lower specification at 25 C. after 12 months for batch 980213A, the results for the other two batches suggest that the lower specification will not be breached after 12 months if stored at 25 C.

The praziquantel content for this formulation varies in the range 96.5–110.0% of label claim of 18.8 g/L for the real time study at 25 C, ambient humidity. The acceptable range of results for praziquantel concentration is 90–110% of label claim. The praziquantel content is not below the lower specification at 25 C. after 12 months.

Conclusion

It can be concluded that the moxidectin and praziquantel oral drench used in this study has maintained a concentration of moxidectin that is above the lower specification at a storage temperature of 25 C. for a period of 12 months. The praziquantel content has been maintained within the specification limits at 25 C. for 12 months.

Example IV

This Example is a comparative study of a formulation produced according to the general method of Example I, but which does not include BHT (other than as present in the concentrate).

| Ingredient | Amount | % Excess | Raw Material Description | Potency | Batch Size 1000 L Requirements % w/v | Batch Size 1000 L Requirements kg |
|---|---|---|---|---|---|---|
| Moxidectin | 0.1% w/v | 5.0 | Moxidectin Concentrate (in benzyl alcohol) | 30% | (0.105) (real) 0.345 | (0.0105) (real) 0.0345 |
| | | | Antifoam 9020 | | 0.005 | 0.0005 |
| | | | Polysorbate 80 USP or equivalent | | 10.000 | 1.000 |
| | | | Disodium Edetate USP or equivalent | | 0.200 | 0.020 |
| | | | Methylparaben | | 0.200 | 0.020 |
| | | | Propylene Glycol USP or equivalent | | 10.000 | 1.000 |
| | | | Polyethylene Glycol 6000 | | 3.000 | 0.300 |
| | | | Polyoxyethylene 40 stearate | | 2.500 | 0.250 |
| Praziquantel | 18.8 g/L | 5.0 | Praziquantel USP or equivalent | 100% | 1.960 | 0.196 |
| | | | Citric acid | | 0.600 | 0.060 |

-continued

| Ingredient | % Amount | Excess | Raw Material Description | Potency | Batch Size 1000 L Requirements % w/v | kg |
|---|---|---|---|---|---|---|
| | | | Sodium Citrate | | 0.250 | 0.025 |
| | | | Propylparaben | | 0.100 | 0.010 |
| | | | Xanthum Gum | | 0.200 | 0.020 |
| | | | Purified Water USP or equivalent | | 70.64 | 7.064 |
| | | | | Total | 100.0 | 10 10L Batch |

Notes:
Adjust quantity of moxidectin added if potency varies from 30% w/v by more than 0.5%

Example V

The Table below shows the stability data after 3 months at a variety of temperatures of the composition according to Example IV. Note that the first figure for each packaging type (i.e. Temperature N/A) is the initial figure.

| Packaging Type | Temperature | Moxidectin (% label claim) | Praziquantel (% label claim) |
|---|---|---|---|
| 100% HDPE | N/A | 105.0 | 105.3 |
| | 25° C. | 92.2 | 102.1 |
| | 30° C. | 87.6 | 99.5 |
| | 40° C. | 81.0 | 102.1 |
| 80% LDPE/20% HDPE | N/A | 105.0 | 105.3 |
| | 25° C. | 89.0 | 101.1 |
| | 30° C. | 85.1 | 105.6 |
| | 40° C. | 79.8 | 98.4 |

Discussion

As can be seen from the stability data in Example V, a combination anthelmintic composition which does not include an additional amount of the antioxidant BHT shows a clear loss of moxidectin stability after 3 months. This can be contrasted with the stability data shown in Examples III for the combination anthelmintic composition including additional BHT, which shows adequate stability after 12 months. Example V also shows that the simple presence of citric acid does not result in adequate stability (citric acid being present in the formulations of Example IV). It may be that the citric acid has a synergistic effect on the additional BHT added (see Examples 1–3) resulting in adequate stability.

The foregoing describes the invention including a preferred form thereof. Modifications and alterations as would be obvious to a person skilled in this art intended to be included within the spirit and scope of the invention disclosed.

What is claimed is:

1. An anthelmintic composition comprising: a first anthelmintic compound which is an Antibiotic S541 or a derivative thereof; a second anthelmintic compound which is insoluble; and an antioxidant which stabilizes the composition, said antioxidant comprising from about 0.15% to about 5.0% by weight of the total composition.

2. An anthelmintic composition according to claim 1 wherein said first anthelmintic compound is moxidectin.

3. An anthelmintic composition according to claim 1 wherein said second anthelmintic compound is praziquantel.

4. An anthelmintic composition according to claim 1 wherein said antioxidant is butylated hydroxytoluene.

5. An anthelmintic composition according to claim 4 wherein said butylated hydroxytoluene comprises from about 0.2% to about 0.3% by weight of the total composition.

6. An anthelmintic composition according to claim 1 further comprising water, wherein said first anthelmintic compound is in solution and said second anthelmintic compound is in suspension.

7. An anthelmintic composition according to claim 6 wherein said first anthelmintic compound is moxidectin, said second anthelmintic compound is praziquantel, and said antioxidant is butylated hydroxytoluene.

8. An anthelmintic composition according to claim 7 further comprising from about 0.1% to about 1.5% by weight of an acid selected form the group consisting of citric acid, phosphoric acid, and a mixture thereof.

9. An anthelmintic composition according to claim 7 further comprising propylene glycol.

10. An anthelmintic composition comprising:
a) moxidectin;
b) praziquantel;
c) an antioxidant which stabilizes the composition;
d) water; and,
e) a glycol.

11. An anthelmintic composition according to claim 10 further comprising from about 0.1% to about 1.5% by weight of an acid selected form the group consisting of citric acid, phosphoric acid, and a mixture thereof.

12. An anthelmintic composition according to claim 11 wherein said antioxidant is butylated hydroxytoluene and said butylated hydroxytoluene comprises from about 0.15% to about 5.0% by weight of the total composition.

13. An anthelmintic composition according to claim 12 wherein said butylated hydroxytoluene comprises from about 0.2% to about 0.5% by weight of the total composition.

14. An anthelmintic composition according to claim 12 wherein said glycol is selected from the group consisting of propylene glycol, polyethylene glycol and mixtures thereof.

15. A method of stabilizing an anthelmintic composition which comprises moxidectin and praziquantel, said method comprising adding butylated hydroxytoluene to said composition in an amount of from about 0.15% to about 5.0% by weight of the total composition.

16. The method according to claim 15 wherein said butylated hydroxytoluene and said moxidectin are both added to the composition as an ingredients of a moxidectin concentrate or moxidectin technical material.

17. The method according to claim 15 further comprising adding to the composition from about 0.1% to about 1.5% by weight of an acid selected form the group consisting of citric acid, phosphoric acid, and a mixture thereof.

* * * * *